(12) United States Patent
Sandrin

(10) Patent No.: US 11,759,178 B2
(45) Date of Patent: Sep. 19, 2023

(54) TRANSIENT ELASTOGRAPHY PROBE WITH SEALING MEMBRANE INTEGRATED TO THE ULTRASOUND TRANSDUCER

(71) Applicant: ECHOSENS, Paris (FR)

(72) Inventor: Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 0 days.

(21) Appl. No.: 17/277,173

(22) PCT Filed: Sep. 16, 2019

(86) PCT No.: PCT/EP2019/074700
§ 371 (c)(1),
(2) Date: Mar. 17, 2021

(87) PCT Pub. No.: WO2020/058188
PCT Pub. Date: Mar. 26, 2020

(65) Prior Publication Data
US 2021/0369242 A1    Dec. 2, 2021

(30) Foreign Application Priority Data
Sep. 18, 2018  (FR) ......................................  1858409

(51) Int. Cl.
*A61B 8/08* (2006.01)
*A61B 8/00* (2006.01)
*A61B 8/12* (2006.01)

(52) U.S. Cl.
CPC ................. *A61B 8/485* (2013.01); *A61B 8/12* (2013.01); *A61B 8/4411* (2013.01); *A61B 8/4455* (2013.01); *A61B 8/4483* (2013.01)

(58) Field of Classification Search
CPC ......... A61B 8/485; A61B 8/12; A61B 8/4411; A61B 8/4455; A61B 8/4483; A61B 8/08; A61B 8/4422
See application file for complete search history.

(56) References Cited

U.S. PATENT DOCUMENTS

| | | | | |
|---|---|---|---|---|
| 4,651,850 A | * | 3/1987 | Matsuo | G10K 11/30 367/153 |
| 9,149,204 B2 | * | 10/2015 | Ehman | A61B 5/0051 |
| 9,622,711 B2 | * | 4/2017 | Zhao | G01N 29/043 |
| 11,160,531 B2 | * | 11/2021 | Sandrin | A61B 8/4455 |

(Continued)

FOREIGN PATENT DOCUMENTS

| | | |
|---|---|---|
| EP | 1 169 636 A1 | 1/2002 |
| EP | 1 531 733 A2 | 5/2005 |

(Continued)

OTHER PUBLICATIONS

Hutchins DA, Robertson TJ, Billson DR, Solanki P. A conical air-coupled capacitance transducer for surface imaging. Ultrasonics. May 2003;41(3):163-73. doi: 10.1016/s0041-624x(03)00098-2. PMID: 12726937. (Year: 2003).*

(Continued)

*Primary Examiner* — Angela M Hoffa
(74) *Attorney, Agent, or Firm* — Pillsbury Winthrop Shaw Pittman LLP

(57) ABSTRACT

A transient elastography probe includes a probe body; an ultrasound transducer configured to generate an ultrasound beam along an axis, the ultrasound beam being generated from a face of the ultrasound transducer; a vibrator located inside the probe body and arranged so as to induce a movement of the ultrasound transducer along a predefined axis; the ultrasound transducer being mounted on the vibrator so that the predefined axis and the axis of the ultrasound beam coincide with each other, and a sealing membrane hugging the outer contours of the ultrasound transducer.

16 Claims, 3 Drawing Sheets

(56) References Cited

U.S. PATENT DOCUMENTS

| | | | | |
|---|---|---|---|---|
| 2005/0203398 A1* | 9/2005 | Sandrin | ............... | A61B 5/0051 600/438 |
| 2008/0058644 A1* | 3/2008 | Sandrin | ............... | A61B 8/0833 600/459 |
| 2012/0271150 A1* | 10/2012 | Ehman | ................ | A61B 5/0051 600/411 |
| 2016/0262706 A1* | 9/2016 | Zhao | ...................... | A61B 5/055 |
| 2018/0140274 A1* | 5/2018 | Sandrin | ............... | A61B 8/4455 |
| 2018/0214913 A1* | 8/2018 | Rus Calborg | ........ | G01N 29/043 |
| 2019/0004015 A1* | 1/2019 | Rus Calborg | .......... | G01N 29/32 |

FOREIGN PATENT DOCUMENTS

| | | | | |
|---|---|---|---|---|
| FR | 2 843 290 A1 | 2/2004 | | |
| JP | S63-294840 A | 12/1988 | | |
| JP | H06-58916 U | 8/1994 | | |
| JP | H11-285496 A | 10/1999 | | |
| JP | 2005-534455 A | 11/2005 | | |
| JP | 2018-519022 A | 7/2018 | | |
| WO | WO 00/55616 A1 | 9/2000 | | |
| WO | WO 2004/016176 A2 | 2/2004 | | |
| WO | WO-2015108666 A2 * | 7/2015 | ......... | A61B 1/00096 |
| WO | WO-2016188947 A1 * | 12/2016 | ........... | A61B 8/4411 |

OTHER PUBLICATIONS

International Search Report as issued in International Patent Application No. PCT/EP2019/074700, dated Nov. 22, 2019.

Notice of Reasons for Refusal as issued in Japanese Patent Application No. 2021-538923, dated May 9, 2023.

* cited by examiner

TRANSIENT ELASTOGRAPHY PROBE WITH SEALING MEMBRANE INTEGRATED TO THE ULTRASOUND TRANSDUCER

CROSS-REFERENCE TO RELATED APPLICATIONS

This application is the U.S. National Stage of PCT/EP2019/074700, filed Sep. 16, 2019, which in turn claims priority to French patent application number 1858409 filed Sep. 18, 2018. The content of these applications are incorporated herein by reference in their entireties.

TECHNICAL FIELD OF INVENTION

The technical field of the invention is that of transient elastography probes and more specifically that of transient elastography probes comprising an ultrasound transducer integrating a sealing membrane.

The present invention relates to a transient elastography probe that may be used for measuring the viscoelastic properties of human or animal tissue and in particular a transient elastography probe comprising an ultrasound transducer provided with a sealing membrane.

TECHNOLOGICAL BACKGROUND OF THE INVENTION

Several hepatic disorders may be diagnosed by evaluating the viscoelastic properties of the hepatic tissue. Chronic viral hepatitis, steatohepatitis of alcoholic and non-alcoholic origin, autoimmune hepatitis, viral hepatitis, primary biliary cirrhosis are all responsible for a progressive change in the stiffness of the liver. In some cases, this increase in stiffness, also called fibrosis, can lead to cirrhosis and to hepatic insufficiency with serious consequences for the patient.

One of the most reliable and efficient techniques for measuring liver stiffness is transient elastography (see for example "WFUMB guidelines and recommendations for clinical use of ultrasound elastography part 3: liver" by G. Ferraioli et al. published in "Ultrasound in Med. and Biol.", 41, 5, 2015).

The applicant has developed and marketed a device known as Fibroscan® (see for example the patents EP1169636 and EP1531733) which measures liver stiffness using an elastography technique known as "Vibration Controlled Transient Elastography" (VCTE), developed by the applicant.

In VCTE applications, the measurement of liver stiffness is based on the measurement of the propagation velocity of transient shear waves inside the tissue under examination. To carry out such a measurement, a particular probe has been developed. This probe comprises at least one vibrator and at least one ultrasound transducer.

For example, in the Fibroscan® probe, the vibrator displaces the ultrasound transducer and pushes it against the body of the patient. This pulsed movement generates a transient shear wave which propagates inside the liver. The displacement caused by the propagation of the shear wave is then probed by sending high frequency, brief ultrasound pulses into the studied medium.

During the examination, the ultrasound transducer is then either directly in contact with the body of the patient or in contact with a water based gel favouring ultrasound transmission. So, the ultrasound transducer has to be water resistant to prevent its deterioration, while enabling an efficient and painless examination for the patient.

SUMMARY OF THE INVENTION

The invention provides a solution to the aforementioned problems, by making it possible to carry out a transient elastography examination that is painless for the patient and with no risk of deterioration of the probe used.

One aspect of the invention relates to a transient elastography probe comprising:
 A probe body;
 An ultrasound transducer configured to generate an ultrasound beam along an axis, the ultrasound beam being generated from a face of the ultrasound transducer;
 A vibrator located inside the probe body and arranged so as to induce a movement of the ultrasound transducer along a predefined axis;
 the ultrasound transducer being mounted on the vibrator so that the predefined axis and the axis of the ultrasound beam coincide with each other, characterised in that it comprises a sealing membrane hugging the outer contours of the ultrasound transducer.

Thanks to the invention, the ultrasound transducer is surrounded by a membrane that makes the probe water resistant thus avoiding damage thereto during the examination. The membrane also makes it possible to cover the angular points on the face of the ultrasound transducer in order to make the examination painless for the patient. Finally, the membrane simplifies obtaining sufficient dielectric insulation for the compliance of the probe regarding the regulations in force.

Apart from the characteristics that have been mentioned in the preceding paragraph, the probe according to one aspect of the invention may have one or more complementary characteristics among the following, considered individually or according to all technically possible combinations thereof.

Advantageously, the ultrasound transducer and membrane assembly constitutes a detachable end piece.

Thus, the ultrasound transducer used may be adapted to the patient, the diameter of the part of the probe in contact with the patient being different according to the morphology of the patient.

Advantageously, the ultrasound transducer has an axis of symmetry corresponding to the axis of the ultrasound beam.

Advantageously, the ultrasound transducer is connected to the probe body by the membrane.

Advantageously, the membrane is made of elastomer.

Thus, the membrane is flexible and deforms when the ultrasound transducer moves.

Advantageously, the membrane is made of silicone type elastomer.

Advantageously, the part of the membrane in contact with the face of the ultrasound transducer forms an acoustic lens configured to focus the ultrasound beam.

Thus, the ultrasound beam is better focused, which makes it possible to obtain more precise measurements. In this case, the part of the membrane located in front of the face of the ultrasound transducer will be convex or concave depending on whether the propagation velocity of ultrasounds in the lens is less than or greater than that of ultrasounds in water.

Advantageously, the part of the membrane in contact with the face of the ultrasound transducer is convex.

Advantageously, the part of the membrane in contact with the face of the ultrasound transducer is concave.

Advantageously, the membrane is made of an electrically insulating material.

Thus, the membrane enables better dielectric insulation of the probe. Indeed, in the existing configuration, it is more difficult to achieve dielectric insulation because the ultrasound transducer is provided with a membrane which covers only the face of the ultrasound transducer. Also, dielectric leakages may occur on the perimeter of the membrane.

Advantageously, the membrane is bonded to the ultrasound transducer.

Advantageously, the part of the membrane which is between the ultrasound transducer and the probe body is deformable.

Thus, the membrane deforms when the ultrasound transducer is displaced under the effect of the vibrator located in the probe body.

Advantageously, the outer diameter of the part of the membrane in contact with the face of the ultrasound transducer is comprised between 3 and 25 mm.

Advantageously, the thickness of the part of the membrane in contact with the face of the ultrasound transducer is comprised between 50 μm and 5 mm.

Advantageously, all or part of the ultrasound transducer has a truncated cone shape, the face of the ultrasound transducer corresponding to the base of the truncated cone of minimum area.

Thus, the surface in contact with the patient is less wide, which makes it possible to accommodate more easily the face of the ultrasound transducer in the intercostal space of the patient while arranging space to accommodate electronic components at the level of a wider rear face.

The invention and the different applications thereof will be better understood on reading the description that follows and by examining the figures that accompany it.

BRIEF DESCRIPTION OF THE FIGURES

The figures are presented for indicative purposes and in no way limit the invention.

DETAILED DESCRIPTION OF AT LEAST ONE EMBODIMENT OF THE INVENTION

Unless stated otherwise, a same element appearing in the different figures has a single reference.

A first aspect of the invention relates to a transient elastography probe. "Transient elastography probe" is taken to mean a probe enabling the implementation of VCTE (Vibration Controlled Transient Elastography) technology, that is to say a probe making it possible to estimate the propagation velocity of a low frequency shear wave in the studied medium using ultra high frequency ultrasound waves to measure local displacements of the medium during the passage of the shear wave. The propagation velocity then makes it possible to estimate a viscoelastic parameter of the medium.

In the remainder of the description, the terms "probe", and "transient elastography probe" will be employed indiscriminately.

Figure 1A:
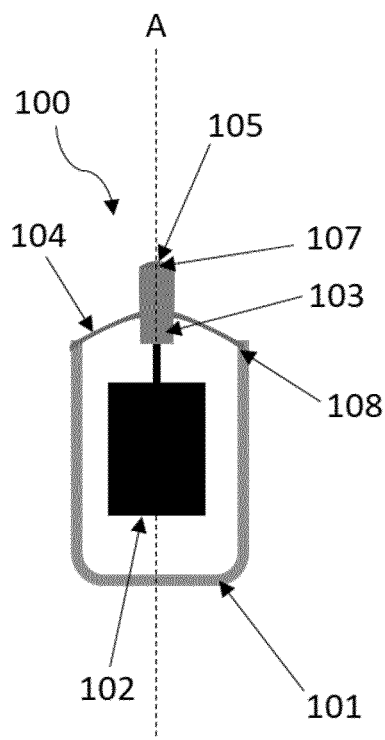
FIG. 1A shows a schematic representation of the transient elastography probe according to a first aspect of the invention.

The probe 100 according to a first aspect of the invention is represented in FIG. 1A.

The probe 100 comprises:
a probe body 101;
a vibrator 102;
an ultrasound transducer 103; and
a membrane 104.

The ultrasound transducer 103 is configured to generate an ultrasound beam. The ultrasound beam is generated at the level of a face 107 of the ultrasound transducer 103.

For example, the ultrasound transducer 103 has an axis of symmetry A. The axis of propagation of the ultrasound beam is then parallel to the axis of symmetry A.

Figure 2A:
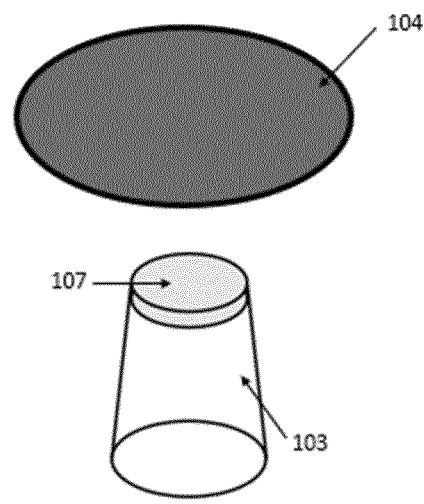
FIG. 2A shows a schematic representation of an ultrasound transducer of conical shape and a membrane of circular shape.

For example, the ultrasound transducer 103 has a truncated cone shape as represented in FIG. 2A or a cylindrical shape and the axis of the cone or the axis of the cylinder is then the axis of symmetry A.

The ultrasound transducer has for example a length greater than 10 mm.

In FIG. 2A, the face 107 corresponds to the small base or base of minimum area of the ultrasound transducer 103 of conical shape. Indeed, a truncated cone has two bases situated in parallel planes, called small base and large base, the small base having an area less than the large base.

In FIG. 1A, the face 107 corresponds to the base of the ultrasound transducer 103 of cylindrical shape which is not in contact with the vibrator 102.

The probe body 101 has a shape enabling the probe 100 to be held in the hand of an operator during the transient elastography examination. For example, the probe body 101 has the shape of a solid of revolution having an axis which is the same as the axis of symmetry A of the ultrasound transducer 103, more specifically the probe body 101 has a cylindrical shape, the axis of symmetry A of the ultrasound transducer 103 being the axis of the cylinder. The probe body 101 then comprises an outer end 108 of circular shape.

The dimensions of the probe body 101 are chosen to enable an operator to hold the probe 100 in his hand. For example, in the case where the probe body 101 is of cylindrical shape, the outer diameter of the probe body 101 is comprised between 20 and 80 mm.

The vibrator 102 is located inside the probe body 101 and the ultrasound transducer 103 is mounted on the vibrator 102.

The vibrator 102 is configured to induce a movement of the ultrasound transducer 103 along a predefined axis which coincides with the axis of symmetry A of the ultrasound transducer 103. This movement makes it possible to push the ultrasound transducer 103 against the body of the patient during the transient elastography examination and thus to generate a low frequency shear wave.

The ultrasound transducer 103 is in contact with the body of the patient at the face thereof 107.

The fact that the conically shaped ultrasound transducer 103 is in contact with the patient at the small base of the truncated cone, as represented in FIG. 2A, means that the face 107 has a smaller surface than a rear face corresponding to the large base of the truncated cone, which facilitates positioning the probe 100 in the intercostal space of the patient while leaving sufficient space to accommodate electronic components at the rear face.

The ultrasound transducer 103 is covered with a membrane 104 which hugs its outer contours and ensures the sealing of the ultrasound transducer 103. For example, the membrane 104 is bonded to the ultrasound transducer 103. The membrane 104 may also be over-moulded on the ultrasound transducer 103.

The fact that the membrane 104 covers the whole of the ultrasound transducer 103 makes it possible to avoid dielectric leakages that occur when the membrane 104 covers only the face 107 of the ultrasound transducer 103.

A part 105 of the membrane 104 covers the face 107 of the ultrasound transducer 103.

The membrane 104 then makes it possible to cover the angular points on the face 107 of the ultrasound transducer 103 to make the examination painless for the patient.

For example, the part of the membrane 104 that is between the probe body 101 and the ultrasound transducer 103 and in particular the part of the membrane 104 intended to be in contact with the patient, is deformable. Thus, the membrane 104 deforms when the ultrasound transducer 103 is displaced under the effect of the vibrator 102 located in the probe body 101.

For example, the membrane 104 is made of an elastomeric material, conferring elastic properties to the membrane 104. More specifically, the membrane 104 is made of silicone.

For example, the membrane 104 is made of an insulating material to ensure better dielectric insulation of the probe 100.

According to an embodiment represented in FIG. 1A, the ultrasound transducer 103 is connected to the probe body 101 by means of the membrane 104.

For example, the membrane 104 has a circular shape and the contours of the membrane 104 are arranged on the perimeter of the end 108 of the probe body 101. The end 108 of the probe body 101 comprises for example a groove making it possible to insert the contours of the membrane 104. The membrane 104 may for example further be bonded or clipped onto the probe body 101.

Figure 1B:
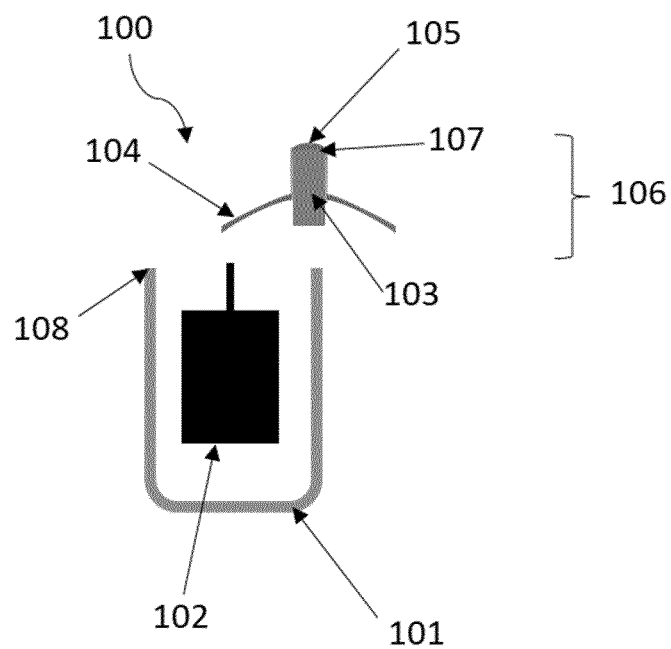
FIG. 1B shows a schematic representation of the transient elastography probe according to a first aspect of the invention from which has been detached an end piece constituted of the ultrasound transducer covered with the sealing membrane.
Figure 2B:
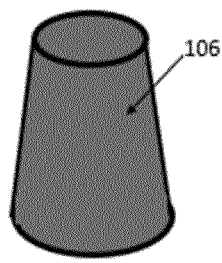
FIG. 2B shows a schematic representation of the ultrasound transducer represented in FIG. 2A covered with the membrane represented in FIG. 2A which constitutes a detachable end piece.

Thus, the ultrasound transducer 103 and membrane 104 assembly is easily interchangeable and constitutes a detachable end piece 106 as illustrated in FIG. 1B or in FIG. 2B.

It is then possible to use end pieces 106 of different sizes to adapt the properties of the ultrasound waves emitted to the morphology of the patient. For example, the end piece 106 may comprise an ultrasound transducer 103 selected among the following ultrasound transducers:

an ultrasound transducer 103 with an 8 MHz central frequency and a 3 mm diameter;
an ultrasound transducer 103 with a 5 MHz central frequency and a 5 mm diameter, the end piece 106 equipped with this type of ultrasound transducer being suitable to measure the elasticity of the liver of children or adults of small size;
an ultrasound transducer 103 with a 3.5 MHz central frequency and a 7 mm diameter, the end piece 106 equipped with this type of ultrasound transducer being suitable to measure the elasticity of the liver of adults;
an ultrasound transducer 103 with a 2.5 MHz central frequency and a 10 mm diameter, the end piece 106 equipped with this type of ultrasound transducer being suitable to measure the elasticity of the liver of obese adults;
an ultrasound transducer 103 with a 1.5 MHz central frequency and a 12 mm diameter.

Indeed, the smaller the diameter of the ultrasound transducer 103 is, the smaller the distance travelled by the ultrasound waves emitted by the ultrasound transducer 103 in the medium is. Thus, in the case of an obese patient, the layer of adipose tissue between the skin and the liver is greater than for a non-obese patient and the diameter of the ultrasound transducer 103 must thus be greater so that the measurements are carried out in the liver and not in the adipose tissue.

The end piece 106 may for example be screwed or clipped onto the probe body 101.

For example, the piece 106 may contain LED type diodes.

The outer diameter of the part 105 of the membrane 104 in contact with the face 107 of the ultrasound transducer 103 is for example comprised between 3 and 25 mm.

The part 105 of the membrane 104 in contact with the face 107 of the ultrasound transducer 103 has for example a thickness comprised between 50 µm and 5 mm.

Figure 3A:
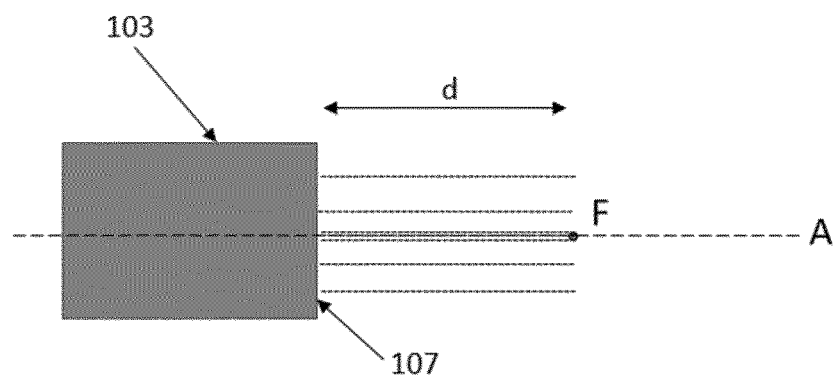
FIG. 3A shows a schematic representation of the ultrasound waves emitted by the ultrasound transducer in the absence of membrane and more particularly the ultrasound waves reflected on a point F located at a distance d from the ultrasound transducer.
Figure 3B:
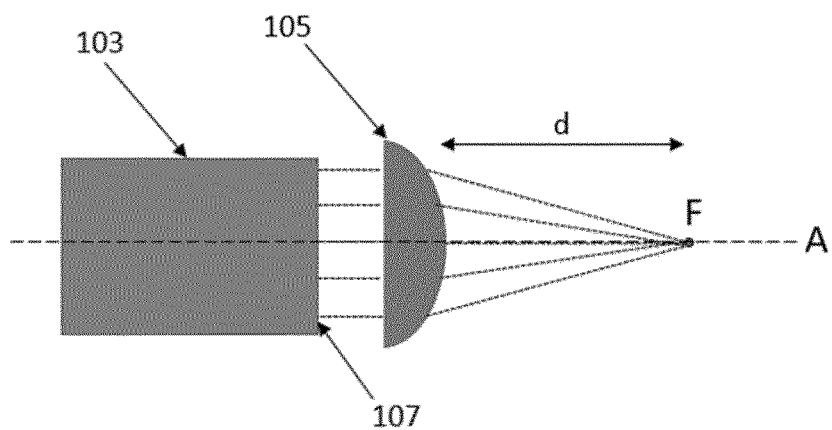
FIG. 3B shows a schematic representation of the ultrasound waves emitted by the ultrasound transducer covered with the membrane constituting an acoustic lens and more specifically the ultrasound waves reflected on a point F located at a distance d from the ultrasound transducer and constituting the focal point of the acoustic lens.

As illustrated in FIG. 3B, the part 105 of the membrane 104 may constitute an acoustic lens capable of focusing the ultrasound beam.

For reasons of clarity, the part 105 of the membrane 104 has been represented as being independent of the ultrasound transducer 103 in FIG. 3B but, in reality, the part 105 of the membrane 104 is in contact with the face 107 of the ultrasound transducer 103.

In FIGS. 3A and 3B, the ultrasound transducer 103 emits an ultrasound beam, the direction of propagation of which is parallel to the axis of symmetry A of the ultrasound transducer 103.

In FIG. 3B, the ultrasound beam is focused by the acoustic lens at a point F located at a distance d from the part 105 of the membrane 104, constituting the focal point of the acoustic lens. All the rays reach the focal point F at the same moment, which is favourable in terms of duration of the diffraction impulse response of the system.

In FIG. 3A, in the absence of the part 105 of the membrane 104, the path of the ultrasound beam is not deviated. The focal point F is defined by the "natural" focusing of the ultrasound transducer 103 of piston type with as drawback that the duration of the diffraction impulse response is greater than by focusing using an acoustic lens.

Figure 3C:
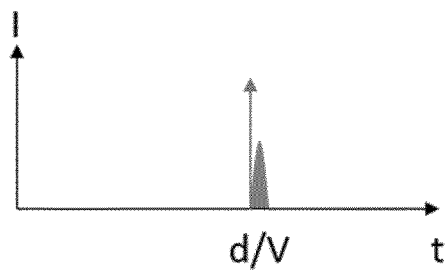
FIG. 3C shows the diffraction impulse response at point F of FIGS. 3A and 3B when the ultrasound transducer is not provided with the membrane and when the ultrasound transducer is provided with the membrane.

In FIG. 3C are represented the diffraction impulse responses at the point F in the case where the ultrasound beam is not focused and in the case where the ultrasound beam is focused at point F by the part 105 of the membrane 104 constituting an acoustic lens. V is the propagation velocity of the ultrasound waves in the considered medium.

It may be noted that the diffraction impulse response at instants close to the instant equal to d/V is shorter in the case of focusing with a lens, which is more favourable to obtaining good axial and lateral resolution of the probe 100.

The intensity of the signal reflected by the point F in the case of the presence of an acoustic lens is also greater than in the case of the absence of acoustic lens since the rays are summated coherently at the focal point F.

The diffraction impulse response at the point F in the case of the absence of acoustic lens is more spread out temporally than in the case of the presence of an acoustic lens because the ultrasound rays do not summate perfectly coherently due to the fact that they travel greater or lesser distances to reach the focal point F.

The acoustic lens may be concave or convex depending on whether the propagation velocity of ultrasounds in the lens is less than or greater than that of ultrasounds in water.

The invention claimed is:

1. A transient elastography probe comprising:
   a probe body;
   an ultrasound transducer configured to generate an ultrasound beam along an axis, the ultrasound beam being generated from a face of the ultrasound transducer;
   a vibrator located inside the probe body and arranged so as to induce a movement of the ultrasound transducer along a predefined axis; and
   the ultrasound transducer being mounted on the vibrator so that the predefined axis and the axis of the ultrasound beam coincide with each other,
   a sealing membrane hugging outer contours of the ultrasound transducer and covering the face of the ultrasound transducer, wherein a portion of the sealing membrane that covers the face of the ultrasound transducer forms a distal end of the transient elastography probe and is adapted to be positioned against a body of the patient,
   wherein a part of the sealing membrane covering the face of the ultrasound transducer forms an acoustic lens configured to focus the ultrasound beam to probe propagation of a shear wave that is generated in the body of the patient by the movement of the ultrasonic transducer against the body of the patient, and
   wherein said sealing membrane is a deformable sealing membrane that deforms during said movement of the ultrasound transducer induced by the vibrator along the predefined axis.

2. The transient elastography probe according to claim 1, wherein an assembly of the ultrasound transducer and the sealing membrane constitutes a detachable end piece.

3. The transient elastography probe according to claim 1, wherein the ultrasound transducer has an axis of symmetry corresponding to the axis of the ultrasound beam.

4. The transient elastography probe according to claim 1, wherein the ultrasound transducer is connected to the probe body by the sealing membrane.

5. The transient elastography probe according to claim 1, wherein the sealing membrane is made of elastomer.

6. The transient elastography probe according to claim 5, wherein the sealing membrane is made of a silicone elastomer.

7. The transient elastography probe according to claim 1, wherein the part of the sealing membrane covering the face of the ultrasound transducer is convex.

8. The transient elastography probe according to claim 1, wherein the part of the sealing membrane covering the face of the ultrasound transducer is concave.

9. The transient elastography probe according to claim 1, wherein the sealing membrane is made of an electrically insulating material.

10. The transient elastography probe according to claim 1, wherein the sealing membrane is bonded to the ultrasound transducer.

11. The transient elastography probe according to claim 1, wherein a part of the sealing membrane which is between the ultrasound transducer and the probe body is deformable.

12. The transient elastography probe according to claim 1, wherein the diameter of the part of the sealing membrane covering the face of the ultrasound transducer is within the range of 3 and 25 mm.

13. The transient elastography probe according to claim 1, wherein a thickness of the part of the sealing membrane covering the face of the ultrasound transducer is within the range of 50 µm and 5 mm.

14. The transient elastography probe according to claim 1, wherein all or part of the ultrasound transducer has a truncated cone shape, the face of the ultrasound transducer corresponding to the smallest base of the truncated cone.

15. The transient elastography probe according to claim 1, wherein a portion of the sealing membrane that hugs the outer contours of the ultrasound transducer and the portion of the sealing membrane that covers the face of the ultrasound transducer form an exterior surface of the transient elastography probe.

16. The transient elastography probe according to claim 1, wherein the sealing membrane covers and is in contact with at least a portion of a lateral surface of the ultrasound transducer, said portion covered by the sealing membrane extending along the predefined axis from said face toward the vibrator.

* * * * *